US010484323B1

(12) United States Patent
Goldstein (10) Patent No.: US 10,484,323 B1
(45) Date of Patent: Nov. 19, 2019

(54) COMPUTER HUMAN INTERACTION AND DIALOG

(71) Applicant: Ira Philip Goldstein, Xenia, OH (US)

(72) Inventor: Ira Philip Goldstein, Xenia, OH (US)

(73) Assignee: iDialogs LLC, Xenia, OH (US)

( * ) Notice: Subject to any disclaimer, the term of this patent is extended or adjusted under 35 U.S.C. 154(b) by 1052 days.

(21) Appl. No.: 14/204,788

(22) Filed: Mar. 11, 2014

Related U.S. Application Data

(60) Provisional application No. 61/778,456, filed on Mar. 13, 2013.

(51) Int. Cl.
| | |
|---|---|
| *H04L 29/06* | (2006.01) |
| *H04L 29/08* | (2006.01) |
| *G06Q 50/00* | (2012.01) |
| *G06F 15/16* | (2006.01) |
| *H04L 12/58* | (2006.01) |
| *G06Q 50/22* | (2018.01) |
| *G06Q 30/02* | (2012.01) |
| *G06Q 10/10* | (2012.01) |

(52) U.S. Cl.
CPC ............ *H04L 51/22* (2013.01); *G06Q 10/10* (2013.01); *G06Q 30/02* (2013.01); *G06Q 50/22* (2013.01); *H04L 29/06* (2013.01); *H04L 51/26* (2013.01)

(58) Field of Classification Search
CPC ....... H04L 51/22; H04L 51/26; G06F 19/345; G06F 19/3475; G06F 19/3481; G06C 50/22; G06Q 50/22; G06Q 10/10; G06Q 30/02; G06Q 99/00; H04W 4/14

USPC ......................................................... 709/206
See application file for complete search history.

(56) References Cited

U.S. PATENT DOCUMENTS

| | | | | |
|---|---|---|---|---|
| 8,001,067 | B2* | 8/2011 | Visel ................. | G06N 3/10 706/23 |
| 8,015,138 | B2* | 9/2011 | Illiff ................. | G16H 15/00 706/46 |
| 8,204,837 | B2* | 6/2012 | Saito ................. | G06Q 30/02 706/12 |
| 8,285,654 | B2* | 10/2012 | Bajrach ............. | G11B 27/105 706/14 |
| 2004/0128359 | A1* | 7/2004 | Horvitz ............. | G05B 19/404 709/207 |

(Continued)

*Primary Examiner* — Kamal B Divecha
*Assistant Examiner* — Clifton Houston
(74) *Attorney, Agent, or Firm* — Wood Herron & Evans LLP (57) ABSTRACT

An algorithm is described that informs a user about the relationship between ongoing measurements and goals for those measurements. For example, it informs a diabetic user whether his blood glucose is outside preset limits. The purpose of the algorithm is to influence the user's behavior so that the measured parameters return to the desired normal range. The algorithm accomplishes this in the following innovative fashion: first, it employs a non-deterministic decision making procedure to select the method of communication. The purpose is to preserve an element of surprise and keep the user interested in the message being delivered. Second, the algorithm varies the emphasis of the message and the time of transmission again to avoid a monotonous sequence of communications. Third, the algorithm is adaptive and adjusts its decision making based on the success or failure of different modalities in affecting the user's behavior.

14 Claims, 13 Drawing Sheets

(56) References Cited

U.S. PATENT DOCUMENTS

| | | | |
|---|---|---|---|
| 2008/0256192 A1* | 10/2008 | Pinard | G06Q 30/02 709/206 |
| 2009/0037413 A1* | 2/2009 | Castell | G06Q 10/107 |
| 2009/0076842 A1* | 3/2009 | Schwarzberg | G06Q 10/10 705/2 |
| 2012/0004924 A1* | 1/2012 | Kachnowski | G06F 19/3481 705/2 |
| 2013/0117371 A1* | 5/2013 | Kim | H04L 51/26 709/204 |
| 2013/0316744 A1* | 11/2013 | Newham | H04M 19/04 455/458 |

* cited by examiner

| Event Object | |
|---|---|
| Field | Description |
| User | Unique user ID |
| Meas DateTime | 2-2-2013 09:19:00 |
| Meas Type | BG, Med[1], Carb, Cal, Insulin, ... |
| Value | Numeric value of measurement |
| Source | Transmitting device, eMail, app[2]. |

[1] Med is a placeholder for the particular medication,
e.g. Metformin, Glyburide, etc.

[2] App is a placeholder for the name of the app that was used.

Figure 5.

| Typical Messages | Pattern Templates | |
|---|---|---|
| Subject: BG 224<br>Body: Ate cheesecake dessert. | Subject: BG <Number?><br>Body: Comment? | 54a |
| Subject: Meds<br>Body: 2 Metformin; 1 Glyburide | Subject: Meds<br>Body: (<number?><med?>)*<br>where med? matches a predefined set of meds | 54b |
| Subject: Breakfast<br>Body: 2 eggs; 3 slices bacon;<br>1 cup coffee | Subject: Breakfast<br>Body: (<number?><food?><br>    <number?><unit?><food?>)*<br>where food? matches a predefined set of foods<br>and unit? matches a predefined set of units. | 54c |

Within Limit Objects report that a current measurement is within an acceptable range.

Outside Limit Objects report that a current measurement is above the Hi Limit or below the Lo limit.

Summary Objects display statistics on a particular measurement over a period of time (last week; last month).

Reminder Objects alert the user to an upcoming event such as the need to refill a prescription.

| Category | Sub-Categories | Object Creation Criteria |
|---|---|---|
| Reminders | Prescriptions, Appointments | Create reminders two weeks, one week and two days in advance of the event |
| Summaries | BG, Calories, Carbs, ... | Create summaries of measurements on a periodic basis (typically weekly and monthly). |
| Limits | Within and Outside Limits for BG, Calories, Carbs, ... | Create reports relating data to limits. |
| Trends | BG, Calories, Carbs, ... | Create reports for when the same condition occurs above some preset frequency. |

| Message Class | Community Average | User Assigned Value |
|---|---|---|
| Text Msgs | | |
| • eMail | 7 | 7 |
| • Instant | 6 | 5 |
| • Pop-up | 5 | 4 |
| Sound Msgs | | |
| • Alarm | 3 | 4 |
| • Ring | 7 | 5 |
| • Voice | 6 | 6 |
| Social | | |
| • Facebook | 4 | |
| • Twitter | 5 | |
| • Family eMail | 5 | |

Figure 16.

where S = sum of the utilities of all Message Leaf classes
and R is a random number generated by the Dialog Manager

Figure 17.

62 —
> Raise emphasis from Medium to High if a trend is observed.
>
> Raise emphasis if messages scheduled for the same time are delivering similar warnings, e.g. High Calorie and High BG.
>
> Lower emphasis for sound messages if the location is a "quiet" location. (This criterion uses Geolocation.)
>
> Raise emphasis if the same report is being communicated a second time.

Figure 18.

| No Trend (64) | Trend (66) |
|---|---|
| If the measurement is more than 20% beyond the relevant limit and there is no trend, then the message should be repeated before the next 3 major events (meals, bedtime, ...). | If the measurement is more than 20% beyond the relevant limits and there is a trend for this kind of measurement, then increase the repetition number from 3 to 4. |
| If the measurement is more than 10% beyond the relevant limit and there is no trend, then the message should be repeated before the next 2 major events (meals, bedtime, ...). | If the measurement is more than 10% beyond the relevant limit and there is a trend, then increase the repetition number from 2 to 3. |
| If the measurement is greater than the relevant limit and there is no trend, then the message should be repeated before the next major event. | If the measurement is greater than the relevant limit and there is a trend, then increase the repetition number from 1 to 2. |
| If the measurement is within bounds, then do not repeat it. | |

COMPUTER HUMAN INTERACTION AND DIALOG

CORRESPONDING APPLICATIONS

The present invention claims priority to U.S. Ser. No. 61/778,456 filed Mar. 13, 2013, which is incorporated herein in its entirety.

BACKGROUND OF THE INVENTION

There are many areas of human behavior where we do not make the best possible choices due to the appeal of certain actions, even when they are not in our best interest. One example is diet: it is in our best interest to avoid obesity, but many people find it difficult to make the decisions that limit their calorie intake to the recommended level. Even those with diabetes whose health is significantly impacted by diet often find it hard to properly manage their calorie and carbohydrate intake during a day. There are many computer systems that generate advice, but they typically use only a small number of methods in their communication. One system relies on email; another on instant messages; a third on pop-up notifications. These systems do not generally vary their mode of communication nor do they learn from experience which modes are most successful.

On the other hand, when people communicate to each other, they use various techniques to be convincing. They may vary the modality of their advice to be effective and to avoid boredom, sometimes employing eMail, sometimes tweets, and sometimes instant messages. They may vary the calligraphy, sometimes employing boldface or capitalization to be more emphatic. They may vary whether others are copied on the message in order to increase pressure on the recipient. As a consequence, personal trainers have proven to be a very effective method for improving individual health; unfortunately, many persons who might benefit from a personal trainer cannot afford the associated cost.

SUMMARY OF THE INVENTION

In accordance with principles of the present invention, a computerized advisory system emulates the flexibility and adaptive behavior people employ when convincing others in order to improve its effectiveness. In its interaction with users, the system selects from among a large number of communication methods. This selection is based on utility functions that are refined as the system is used. The methods include communicating with the user via text, graphics, and sound. They also include communicating with intermediaries to further motivate the user. Furthermore, the system's communication choices are non-deterministic. This preserves an element of unpredictability which increases the individual's attention to the messages. Finally, the system improves its effectiveness over time by tracking the consequences of its messages and adjusting the utility associated with each method to better reflect its effectiveness.

In the particular embodiment described herein, the advisory system is used for diabetes management. Diabetes management generally involves a number of activities undertaken by diabetics to track their medications, exercise and diet in order to successfully control their own blood glucose levels. However, there are many other applications for the principles of the present invention such as weight loss, exercise programs, blood pressure management, and remediation of addictions such as alcoholism and other addicting substances.

As presented herein, the invention features a system for generating communications with a human user, those communications generally in the form of notifications regarding measured quantities of interest to the user, and the relationship of those quantities to goals and limits, wherein the system selects a message technique for communications in a non-deterministic fashion, based upon a utility value for plural available message techniques.

In the described particular embodiment, the system implements an adaptive process to improve the effectiveness of its advice, by causing its probabilistic selection criteria for message types to be adjusted in response to past successes and failures. The system initializes its probabilistic selection criteria for a communication method (mail, instant message, alarm, tweet,) based on the average values of these probabilities for other users of the system. The algorithm is further adaptive, i.e. improves the effectiveness of its advice, by adjusting its probabilistic selection criteria based on the criteria employed by agents for other users.

In the particular embodiment, the system moderates the potential overflow of messages to a user by placing messages in a queue and applying rules to prune that queue by combining messages or cancelling messages.

In the particular embodiment the system adjusts the choice of message and level of emphasis in the body of the message based on trends in the relationship of measurements to pre-set limits, becoming more emphatic when negative data trends are identified.

The system further increases the effectiveness of its communication by selecting friends and family as collateral recipients of out-of-range and in-range messages. This selection is also done in an adaptive manner, modifying the probability of using these techniques based on their effectiveness.

The system increases the effectiveness of its communication by selecting alternatives to direct communication such as tweets to a community or posting on Facebook in an adaptive manner, modifying the probability of using these techniques based on their effectiveness.

In the specific described embodiment, geolocation is used in controlling the communications from the system. Specifically, the system switches to quiet communication based on the location of the recipient, employing techniques such as vibration in those situations. Geolocation and calendar access are also used to determine whether the user is in a hands-busy environment. In hands-busy environments (e.g. driving a car) where the user cannot look at the screen of his personal communications device, the system employs non-verbal communication (alarms, ringtones, vibrations) as alternatives to written or voice communication, adjusting the probability of such communication techniques based on past experience.

Although principles of the present invention are applicable to a number of different environments, in the specific application of the invention to diabetes management, the algorithm adapts its warning messages regarding blood glucose limits based on the effectiveness of past messages in controlling the user's blood glucose.

The above and other objects and advantages of the present invention shall be made apparent from the accompanying drawings and the description thereof.

DETAILED DESCRIPTION

The following description presents an overall system that collects data and communicates with a user. This system, illustrated in FIGS. 1 and 2, will be referred to as IDA, which is an acronym for Intelligent Digital Agent. IDA is a 7 day a week, 24 hour a day, server-based system that resides at an Internet site. The system carries out data collection and communication processes in three steps.

Figure 1:
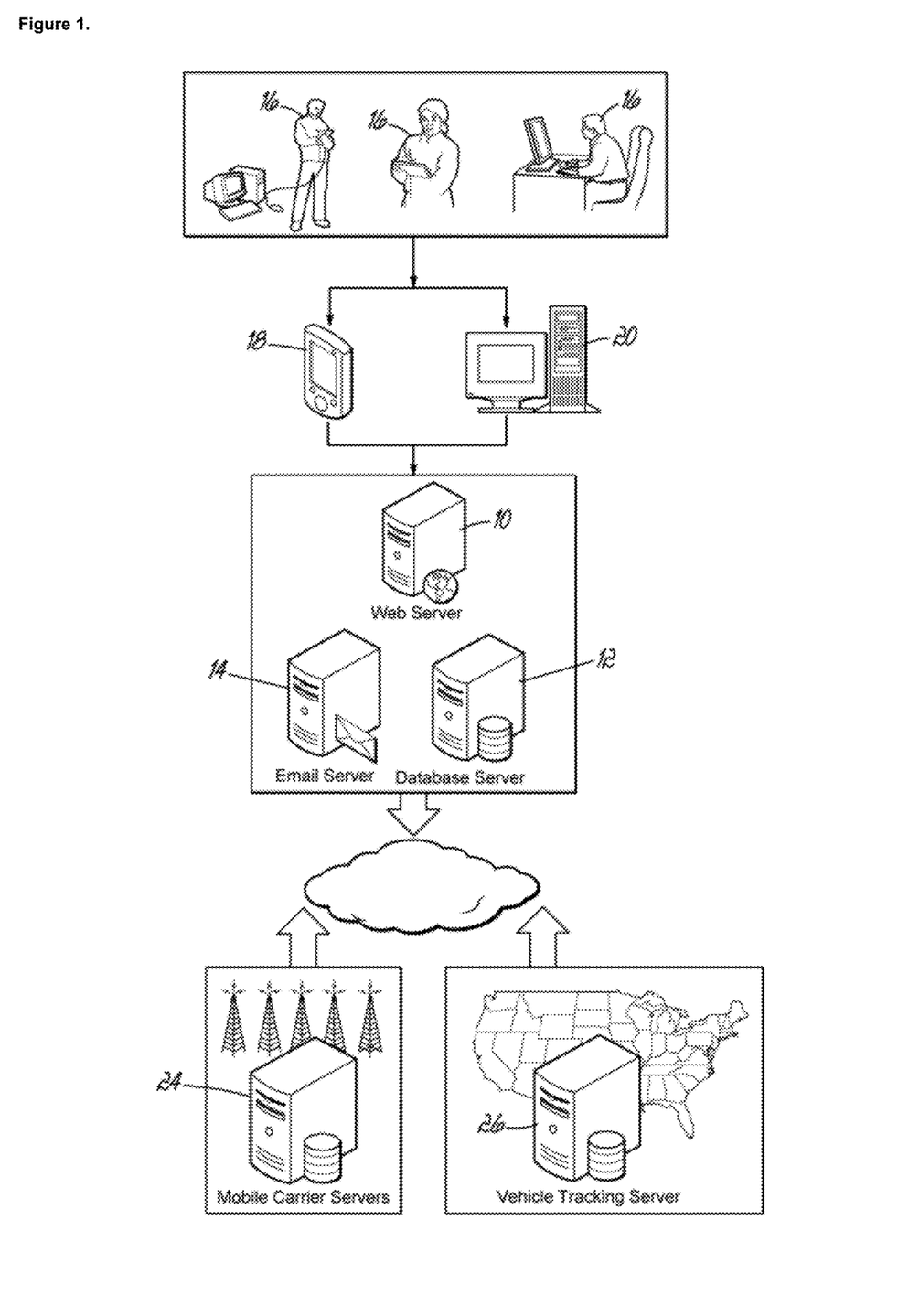
FIG. 1 illustrates a user of the service contemplated herein, connecting through a portable device or computer to a web server, mail server or other communications point, to a computer or computer network implementing the invention, which includes the communications servers and a database server, and systems for receiving and transmitting notifications of activities of a user.

Referring now to FIG. 1, an exemplary environment for implementation of the present invention includes a web server 10, in communication with a database server 12 and email server 14. As elaborated below, database server 12 stores records of Events, Reports and Messages, as well as criteria to be compared to Events to determine when Messages should be generated and the form thereof. Interaction with the database is via web server 10 and via email server 14, which transmits the notices referenced herein and receives emails from the user, and may also be utilized in a process for establishing and maintaining a user account by association of the user with a unique email address, which can be confirmed by the delivery of a confirming URL via email to that email address.

A user 16, such as a responsible person or potentially a monitored person accesses information from web server 10 via a mobile device 18 and/or computer 20 which may be a desktop, laptop or palmtop computer. Mobile web pages or custom applications for mobile devices may be used with equal effect to interact with the system and obtain Messages. Other functions available through the web server may include accessing historical records of Events of and viewing User profiles and Messages for the purpose of analyzing and identifying the activities of the system and improving the same.

The system may also be coupled via the Internet to mobile carrier servers 24 and/or Vehicle Tracking Servers 26 which can provide geolocation information regarding the user 16, which is useful in various manners as described in detail below.

Figure 2:
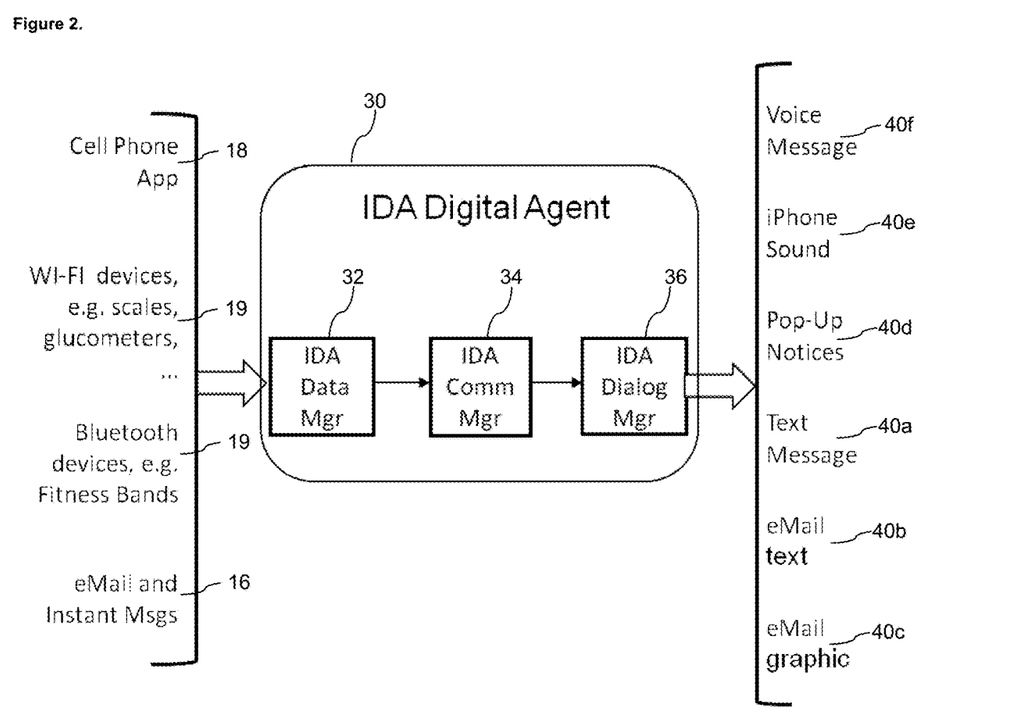
FIG. 2 illustrates a three step process used for communicating with a user.

Referring now to FIG. 2, IDA 30 comprises three components: First, the Data Manager 32, which collects input from the user and from Internet-ready devices. Second, the Communications Manager 34, which identifies information to be communicated to the user. Third, the Dialog Manager 36, which decides how to accomplish these communication tasks, choosing, for example, the level of emphasis and the medium for the output (text message 40a, email 40b, email with graphical content 40c, instant message or other forms of pop-up notifications 40d, event-related sounds 40e, and/or voice messages 40f).

Figure 3:
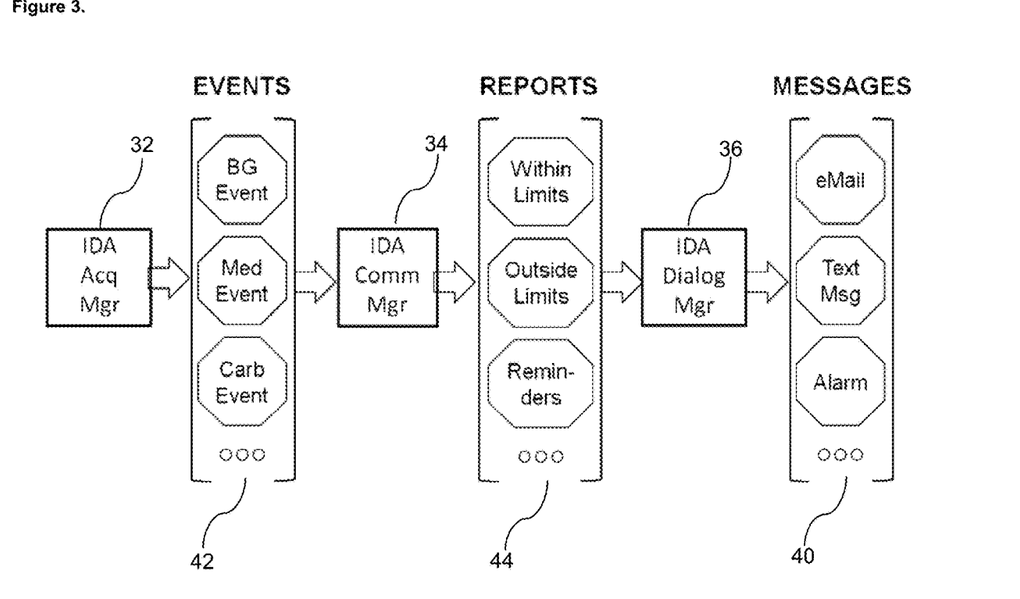
FIG. 3 illustrates the event, report and message objects built by the system as it constructs feedback for the user.

As seen in FIG. 3, the flow of these steps and the control thereof is described herein in terms of the data objects created at each stage. These include events 42 generated by the Data Manager 36 in response to communications from the user 16, Reports 44 generated by the Communication Manager in response to Events, and Messages 40 generated by the Dialog Manager in response to Reports.

The three steps illustrated in FIG. 3 are now described in order in greater detail.

Data Manager

Figure 4:
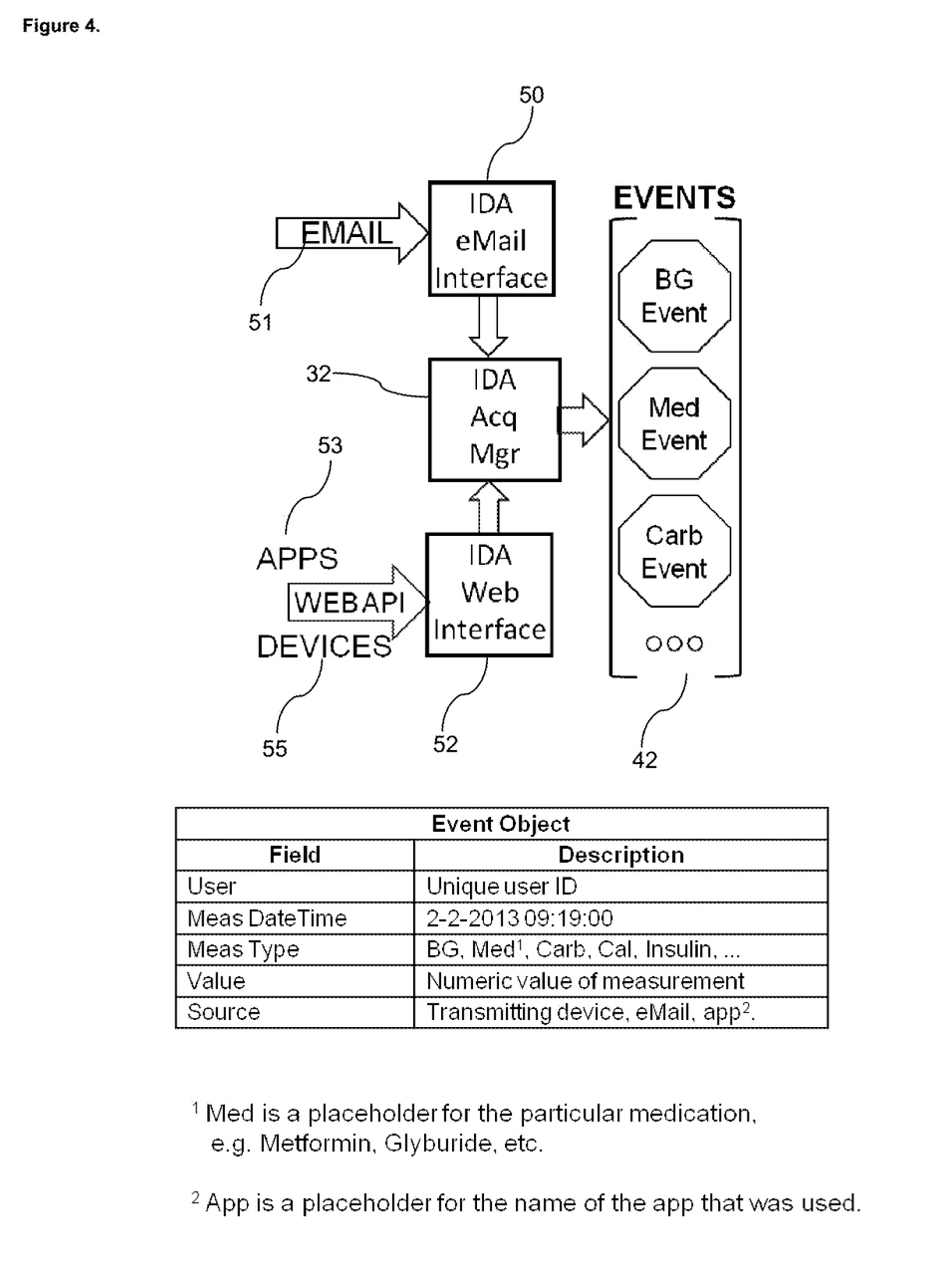
FIG. 4 illustrates event objects created by the data manager to describe incoming measurements from the user.

The first step is carried out by the Data Manager 32. Referring now to FIG. 4, the Data Manager 32 collects measurements and user comments that are relevant to subsequent communication, via an eMail interface 50 and Web interface 52. For a diabetes application, this data includes blood glucose (BG) measurements, dosages of insulin and other medications, diet and exercise. As seen in FIG. 4, data may be collected directly from Internet-capable devices 55 or from the user via eMail 51 or via applications 53 running on a local device such as a smart phone, tablet or PC. As this information is added, the Data Manager creates Event Objects seen in FIG. 4, such as BG event, a Medication (Med) event, and a Carb (food consumption) event.

The Data Manager's web interface uses standard Internet protocols to receive data from devices directly or from servers connected to those devices. For example, the Withings scale supports the REST Internet protocol. The scale reports to the Withings server which in turn interacts with the IDA Web Interface via the REST protocol. An App on a Smart Phone can directly interact with the IDA Interface via web services supported by the phone's operating environment.

The IDA eMail Interface 50 shown in FIG. 4 retrieves messages from iMAP and POP accounts. For example, messages sent to IDA@iDialogs.com are retrieved using iMAP. The eMail Interface 50 then parses the Subject and Body of the message to extract data and comments. The parsing is done by matching regular expression templates against these fields.

Figure 5:
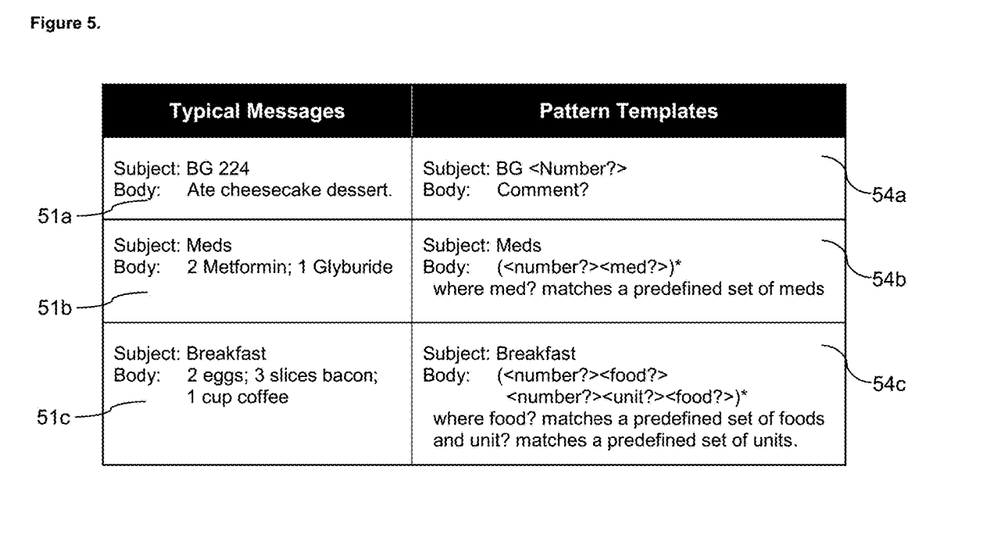
FIG. 5 illustrates typical messages and corresponding pattern templates utilized by the system.

FIG. 5 shows some typical email messages 51a, 51b, 51c delivered to data manager 32 and the corresponding pattern templates 54a, 54b, 54c. (The FROM, TO, and DATETIME fields of eMail messages are not shown but their data is also extracted. There is no pattern matching issue with respect to those fields; so the extraction is straightforward.) FIG. 5 illustrates BG, Medication and Food related emails 51a, 51b and 51c respectively, and the pattern templates 54a 54b, 54c respectively which match to them.

Figure 6:
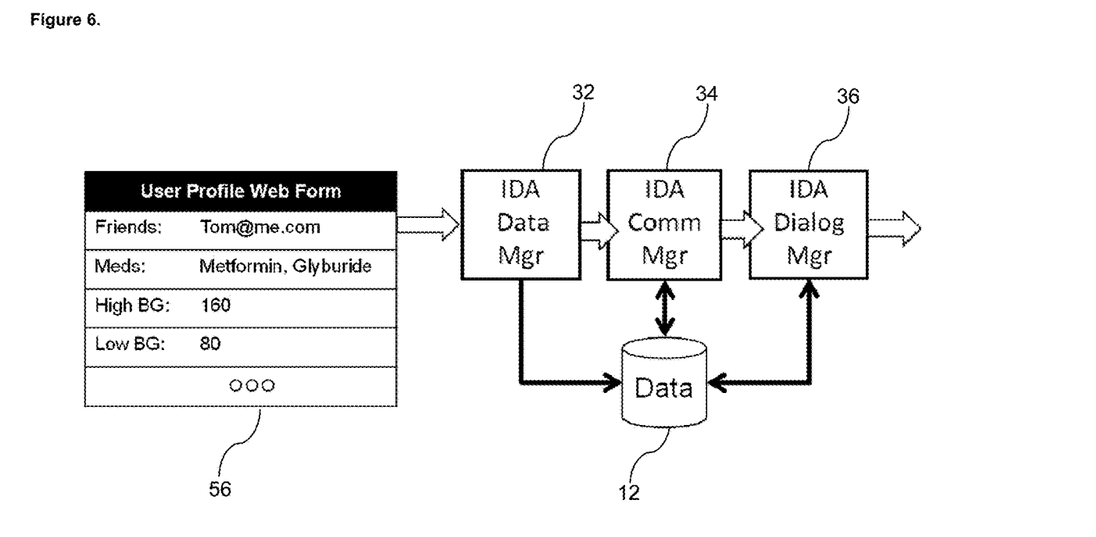
FIG. 6 illustrates user background information entered via web form and stored in the database utilized by the system.

As seen in FIG. 6, user background information is also stored in the database. This background information 56 includes such topics as addresses of friends and family for social communication and future medical appointments, prescribed dosages of medications, high and low limits for measurements, and other relevant information to the specific application to which the IDA 30 is used. Web forms presented by the Data Manager 32 are used to obtain this information from the user, which is stored in database server(s) 12.

Communications Manager

Figure 7:
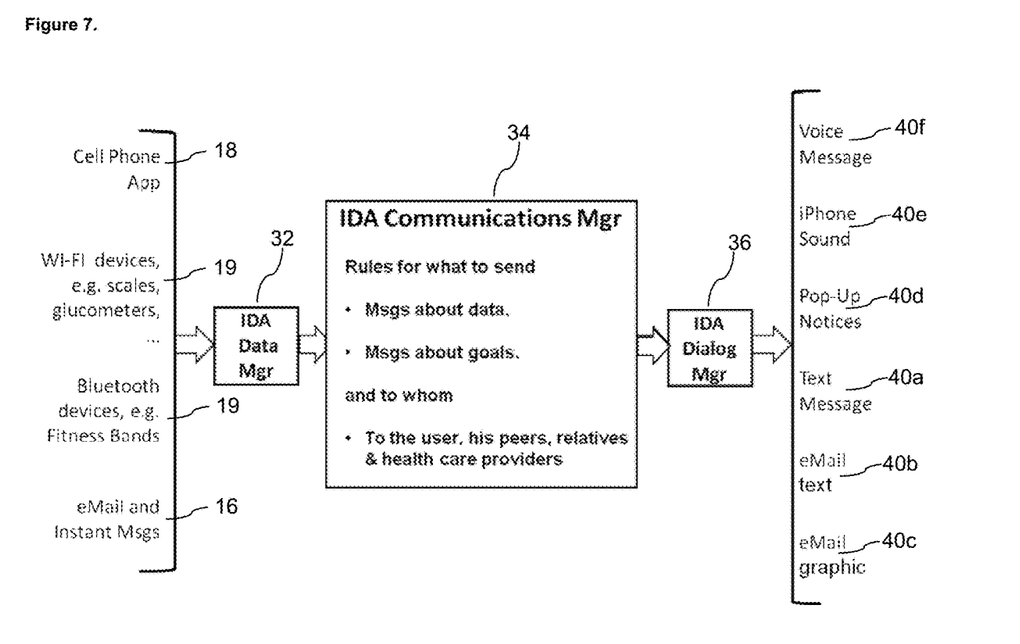
FIG. 7 illustrates the operation of a Communications Manager which determines the reports to be sent by the system.

Referring now to FIG. 7, the Communication Manager 34 employs procedures that determine what information to send and to whom. This is the second in the overall process performed by IDA. Note that decisions about when to send the message 40a-40f, what modality to use and other similar considerations are not made by the Communication Manager 34; such choices are the province of the Dialog Manager 36 and occur in the third step.

Figure 8:
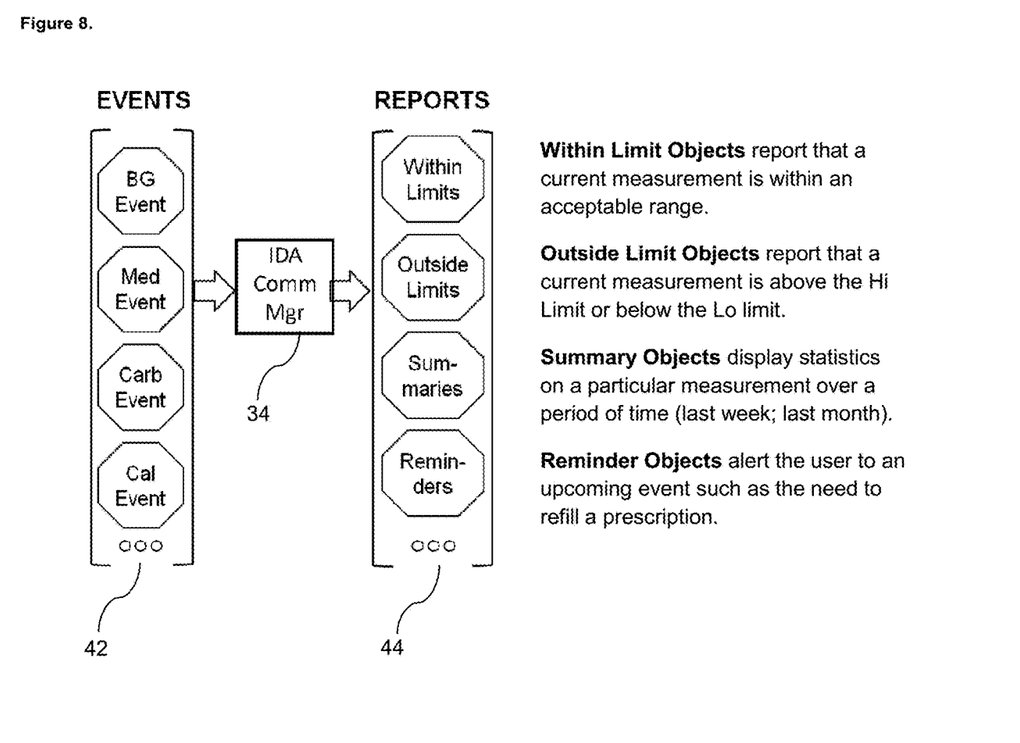
FIG. 8 illustrates the creation of Report Objects by the Communications Manager using events from the user.

As shown in FIG. 8, the Communication 34 Manager produces Report Objects 44 in response to Events 42; these Report Objects 44 embody the decisions made by the Communication Manager 34 as to what should be communicated to the user based upon recent events. Reports may include a Within Limits Report Object that a current measurement is within an acceptable range, an Outside Limits Report Object that a current measurement is above the Hi Limit or below the Lo Limit for the user, a Summary Report Object that displays statistics on a particular measurement over a period of time such as the last week or last month, and a Reminder Report Object that alerts the user to an upcoming event such as the need to refill a prescription medication.

Figure 9:
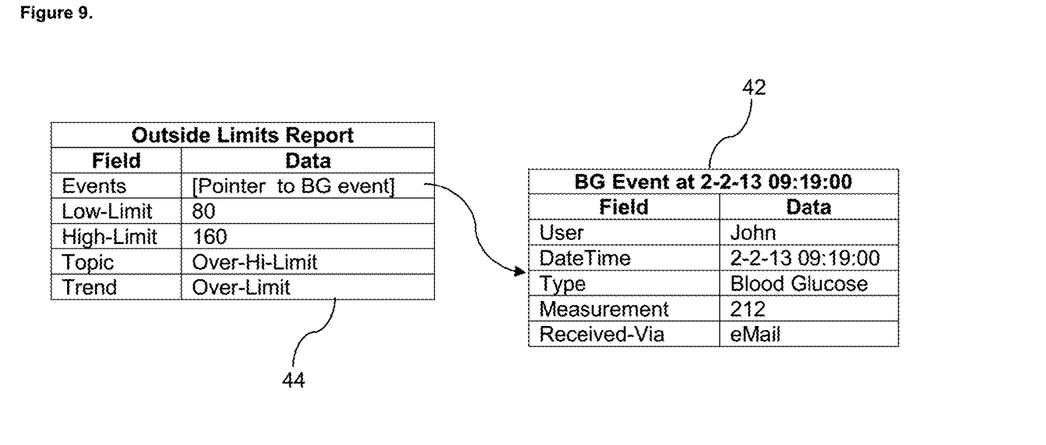
FIG. 9 illustrates a Report Object that informs the user that the Hi Limit has been exceeded.

FIG. 9 illustrates an exemplary Outside Limits Report Object 44. The topic of the report object is that a BG measurement has exceeded the limit supplied by the user. The Report Object contains a pointer to the relevant data event 42 (from which some information in the report object 44 is derived), information about the user-supplied limits retrieved from other tables in the database and the topic. (For each topic, the database stores templates for the actual text of the message.) The Trend field indicates the existence of a recurring set of measurements outside the desired limits.

For most blood glucose management applications, an over limit condition would create an immediate message to the user. For traditional meters, the message would be displayed on the meter's screen. Some meters which are connected directly to cell phones may display the message on the cell phone itself. A few Internet-connected meters are available which might be capable of generating an eMail message, but there would be no variation in that message. In contrast, in the IDA system, the report 44 is determined separately from decisions about when to communicate it, how emphatic to make that communication, and what modality to use. These decisions are made by the Dialog Manager 36 in the third step of the communication process and will be described in the next section.

Figure 10:
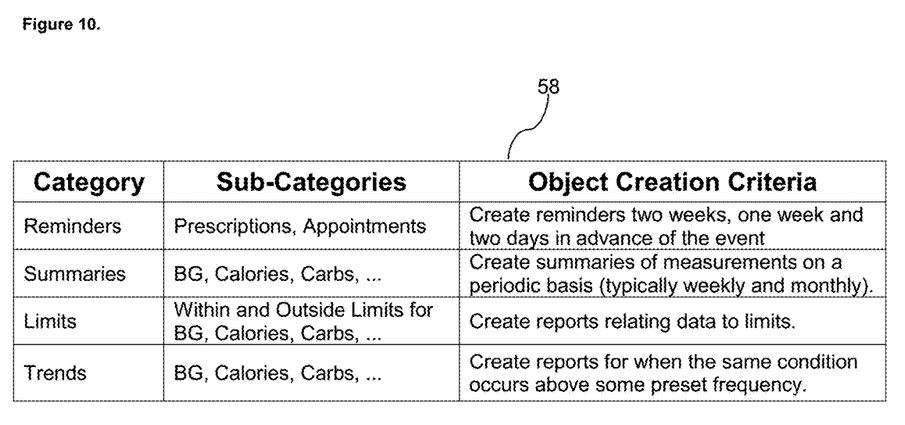
FIG. 10 illustrates criteria used by the system for creating Report Objects.

FIG. 10 summarizes the object creation criteria 58 for various categories of Report Objects. As shown there, Reminders are generated, for example, two weeks, one week and two days in advance of an event, Summaries are created on a period basis such as weekly or monthly, Limits reports are created when there is data relating to limits, and Trends reports are created when the same condition re-occurs above a preset frequency.

Once created, the Report Objects 44 are sent to the Dialog Manager, which is described in the next section.

The Dialog Manager

Figure 11:
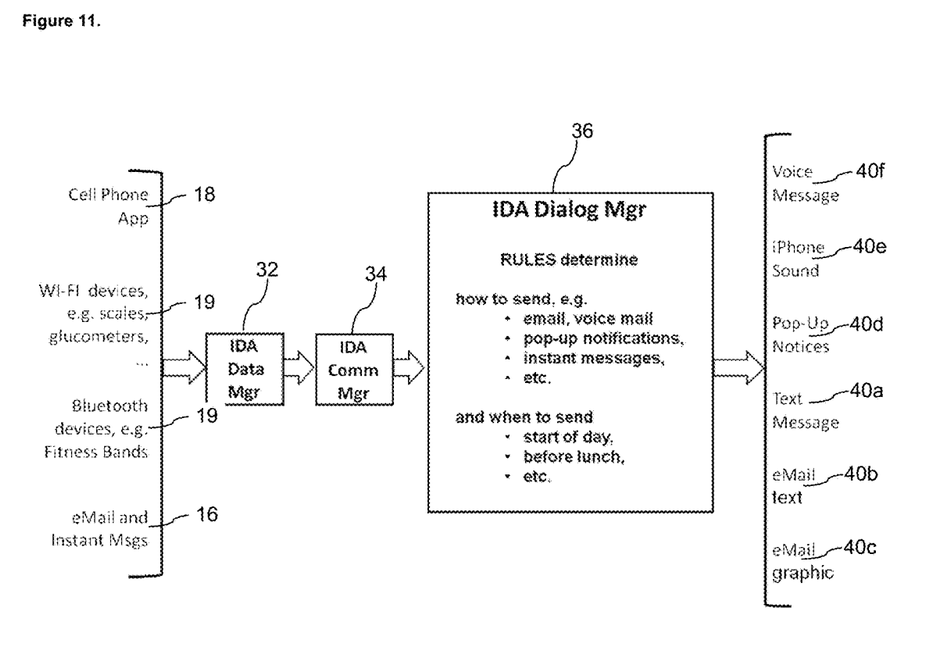
FIG. 11 illustrates the operation of the Dialog Manager in deciding how, when and to whom to send a message.

FIG. 11 illustrates the functions of the Dialog Manager 36, which generally makes decisions about the mode of communication of the substantive information in Report Objects 44. Modes of communication may include eMail 40a, voice messages 40f, Facebook or other social network postings 40d, instant messaging 40a via SMS/cellular messaging, networks such as Twitter, Skype, Facebook or Microsoft Messaging or the like. The Dialog Manager 36 further determines recipients, time of delivery, and level of emphasis for reports, as well as other factors which can be adapted to accomplish an impact on the user.

Figure 12:
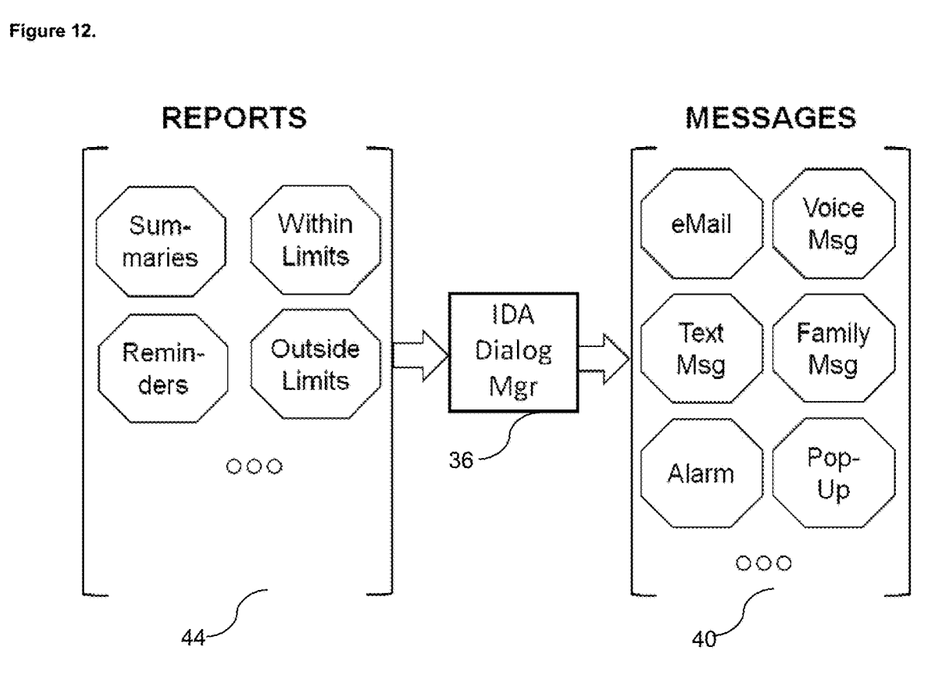
FIG. 12 illustrates the selection of a Message Object by the Dialog Manager to communicate each report.

FIG. 12 illustrates the operation of the Dialog Manager 36, which begins by selecting a Message Object 40, where each Message Object represents a different communication mode.

Figure 13:
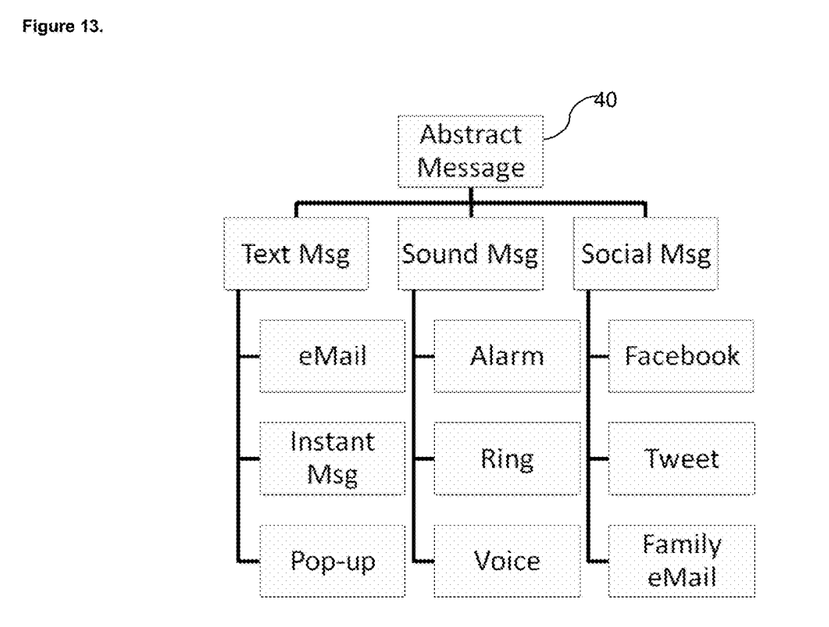
FIG. 13 illustrates a hierarchy of message classes, each class representing a different communication method.

As shown in FIG. 13, Message Objects 40 are instances of a class hierarchy that represents a broad range of communication strategies. This is an extensible hierarchy and additional classes can be defined. For example, classes for secure and unsecure messages might be defined or classes for different kinds of Instant Messages. The more important fields that are defined in the Abstract Message class are shown in the table presented below:

| Field | Purpose |
| --- | --- |
| User | The ultimate recipient |
| Via | The intermediary (if any) such as the user's wife. |
| When | The time to send the message, e.g. before lunch. |
| Emphasis | How emphatic to make the message (High, Med, Low) |
| Previous Repetitions | How many times has this same message been sent |

More specific Message classes contain additional fields for describing the details of their kind of communication. For example, the Alarm class would contain fields for the sound file employed and its volume while the Phone class would contain fields for the phone numbers to use.

Figure 14:
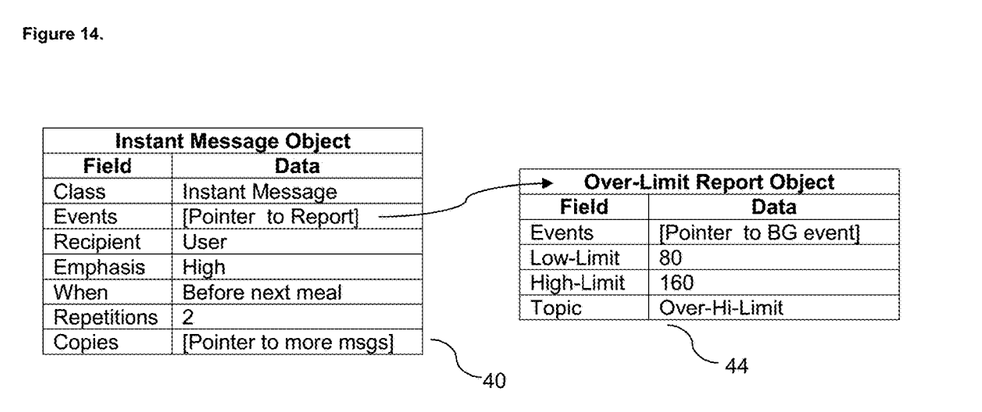
FIG. 14 is an exemplary illustration of an instant message transmitting an "over-limit" report.

FIG. 14 provides an example of an Instant Message class object 40d, being employed to transmit content from an Over-Limit report 44. The emphasis is High and the scheduled time is before the next meal, to assist the user in remediating the over limit condition.

The Message Class, or more precisely, a leaf node in the Message class hierarchy, is selected using an adaptive, non-deterministic algorithm. The non-determinism is introduced to insure that the system is not repetitive in the manner in which it communicates with the user. The adaptive behavior is achieved with a feedback loop designed to make effective communication modes more likely to be selected.

The decision algorithm is based on utility numbers which are defined for each class either directly or inherited from a super-class. These numbers range from 0 to 10. The initial values are set when a user completes his "User Profile".

Figure 15:
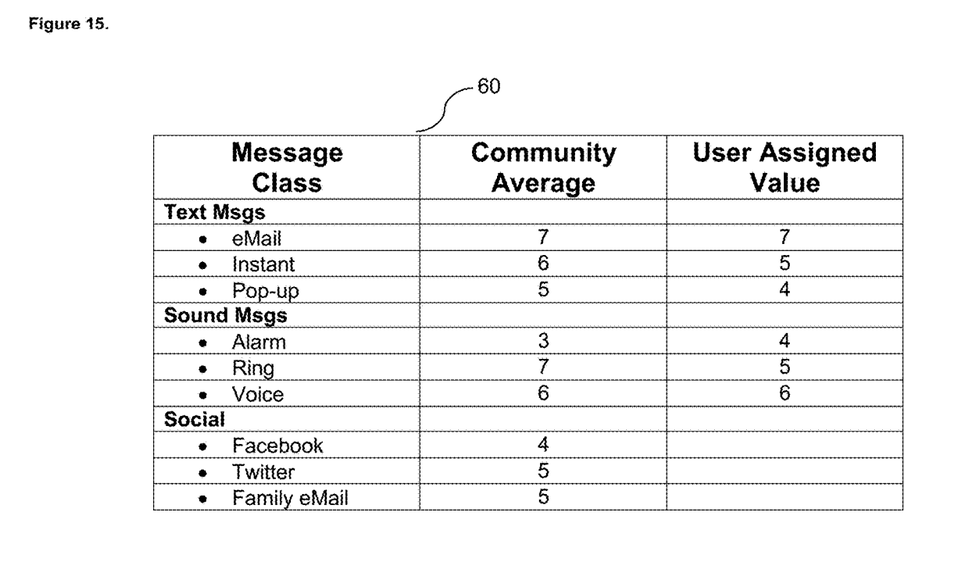
FIG. 15 illustrates a User Profile used by the Message Utilities in which Community Averages, used as defaults, have been overridden by user-specific assigned values.

FIG. 15 provides an example table 60 storing utility numbers for various message classes. Default values for message classes are obtained by using a community average of an applicable community to which the user belongs, which may be an age-related group, geographic location-related group, or other demographic. Since the system is cloud-based, Dialog Manager 36 can obtain this average across its user community or a subset thereof, and update it dynamically. Community averages for utility numbers are used if the user does not explicitly provide a preference. In the example shown in FIG. 15, there is no user assigned value for Social message classes and accordingly default values are used.

Figure 16:
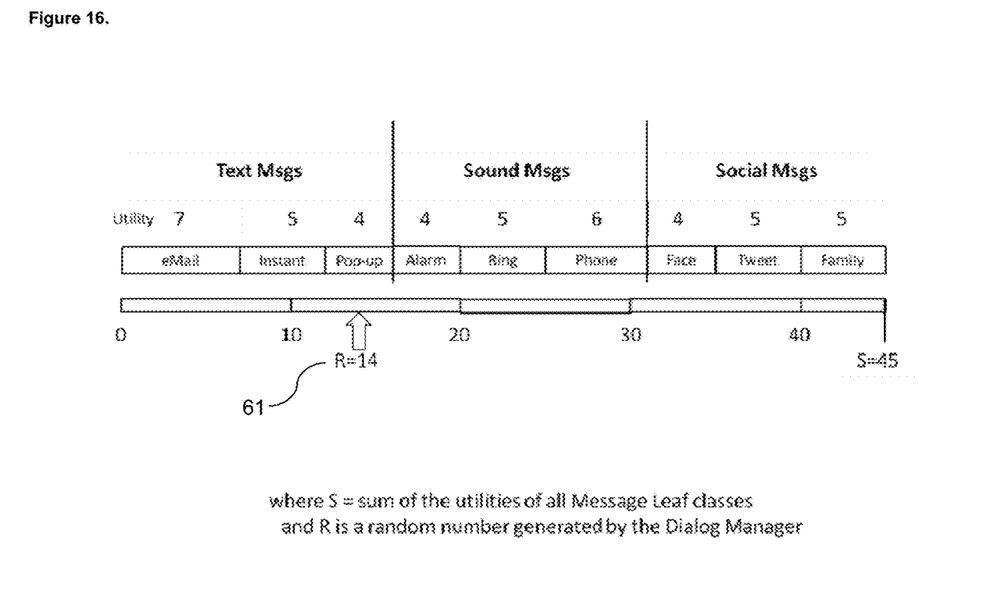
FIG. 16 is a number line illustration showing the utilities metrics for each message class.

FIG. 16 illustrates the method by which the Dialog Manager 36 chooses a message class for a given message. FIG. 16 illustrates a conceptual mapping in which each messaging class is presented as a blocks along a number line, with each class represented by a block equal in size to its utility number; the number line extends from 0 to S, where S is the total of all message leaf utility numbers. To choose a messaging class, the Dialog Manager 36 generates a random number C 61 between 0 and S. C will fall into one of the intervals on the number line, and in response, the message class associated with that interval will be selected as the method for communicating with the user.

For example, if C=14, it will fall into the POP-UP interval in FIG. 16, and as a consequence that method will be selected for communicating with the user. A message object M that is an instance of the selected class is then created and its remaining fields are determined as discussed below.

Figure 17:
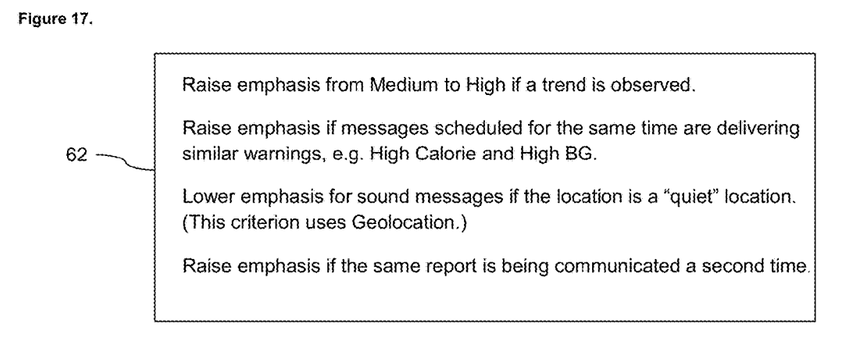
FIG. 17 illustrates typical criteria used to determine whether emphasis should be High, Medium or Low.

The Emphasis field is used by the Message class to determine such factors as the volume of sound and choice of ringtone for Sound Messages and the size and face of fonts for Text Messages. For a given emphasis value, the actions taken are defined by methods specific to the message class. Starting with a default emphasis value of Medium, the Dialog Manager 36 uses the criteria 62 such as shown in FIG. 17 to adjust the emphasis to High or Low. Specifically, emphasis is raised from Medium to High if a trend is observed, or if messages scheduled for the same time are delivering similar warnings such as High Calorie count and High BG. Emphasis is lowered for sound messages if the user is in a "quiet" location as determined by geolocation of the user's device. Emphasis is raised if a report is being communicated for a second time, e.g., two over-limit messages in a row.

Figure 18:
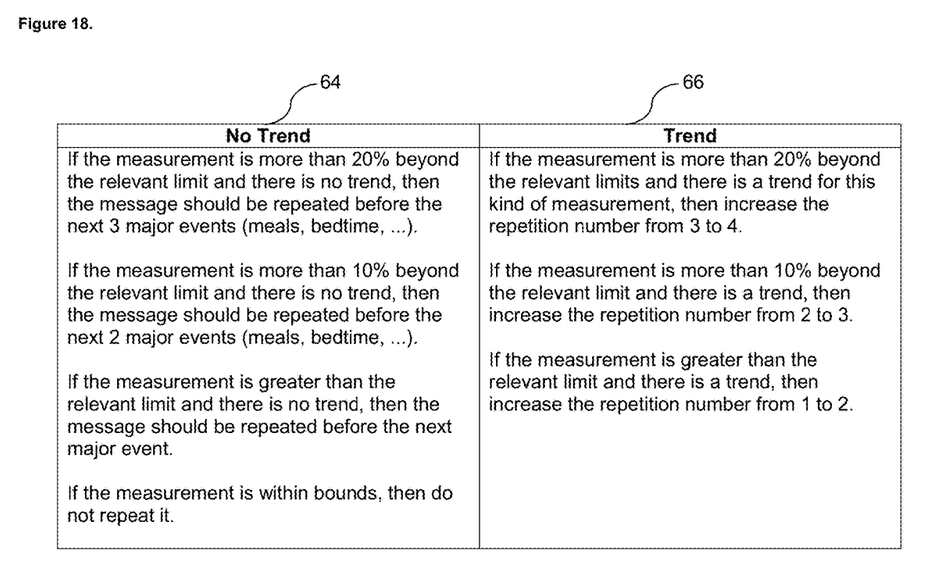
FIG. 18 illustrates rules used to determine the number of repetitions of messages to the user.

FIG. 18 illustrates criteria used by Dialog Manger 36 to set scheduling of a message. The default times to transmit a message are immediately upon the data arriving, and one repeat transmission before the next major event (meal, exercise, bedtime). The presence of a trend (64) or absence of a trend (66) affects whether the message is repeated, based upon the nature of the message as elaborated in FIG. 18. As illustrated, severe divergences result in more frequent repetitions of the message. A Within-Bounds message, on the other hand, would not be repeated.

Transmitting the Message while Avoiding Excessive Communication

After all of the fields of message object M have been determined, the Dialog Manager 36 then instructs the Message object to transmit its message. The transmission procedure is defined in the associated class and takes account of the values of the emphasis fields, trend fields, limit fields and other data stored in the object.

However, there remains one last refinement. The system is at risk of generating too many communications with the user, thereby weakening the impact of these communications. This can convert the system's strength in generating messages into a weakness. To avoid excessive interaction, the Dialog Manager 36 places all messages in a queue. Dialog Manager 36 then analyzes the queue before actually transmitting messages. In some circumstances, the Dialog Manger 36 combines messages if certain criteria are met. Examples of the criteria used to combine messages M1 and M2 into a combined message M3 are as follows:

1. M1 and M2 are conveying similar kinds of material, i.e. graphic, text, voice.
2. The resulting message is not too long, where maximal lengths are stored in various message classes.
3. M1 and M2 are similar kinds of reports, e.g. both are over-limit reports.

As with the utility numbers discussed earlier, this behavior is adaptive as the system can observe whether certain message combinations correlate with improved behavioral measurements. The likelihood of applying a messaging rule is increased if a positive correlation is found. In order to have a large enough sample, this correlation is computed across the entire user community.

The system can also employ limits on the number of messages sent in a given period and only transmit high priority messages. The priority of a message is stored in its class definition. For example, outside-limit messages have a high priority while event reminders have a lower priority. The user can set guidelines for the number of messages that are acceptable in his User Profile.

Adaptive Behavior

The system according to the present invention is adaptive—i.e. the utility metrics associated with Message classes are changed by the system over time based on experience. Specifically, the system changes the utility of a Message class based on its success, where success is measured by whether certain data measurements improve. Examples of such data measurements are BG readings, calories burned during exercise and calories consumed from meals.

Figure 19:
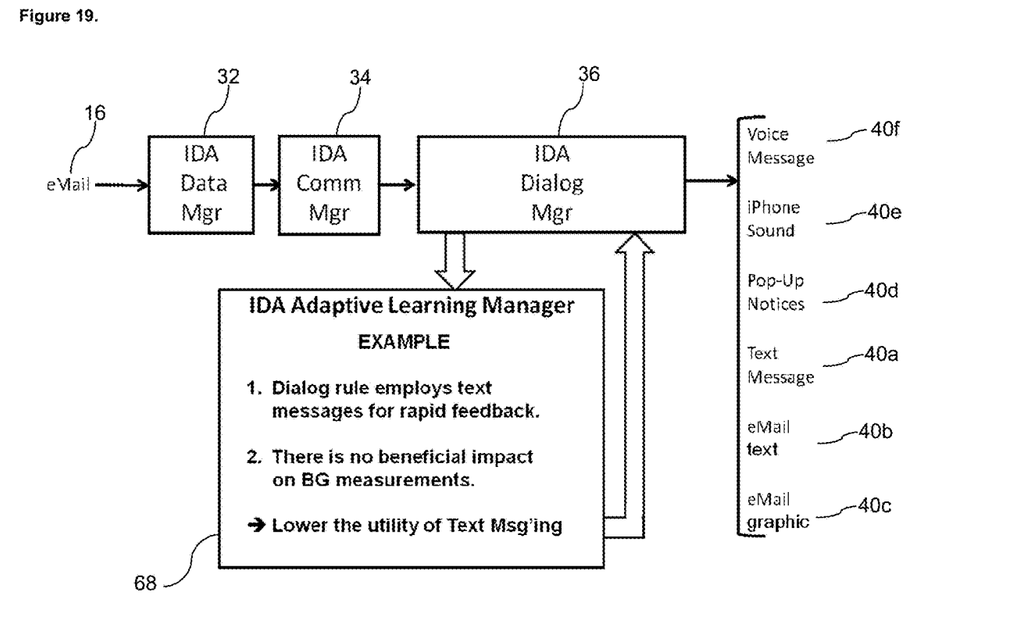
FIG. 19 is an illustrative example of adaptive behavior of the system in the assignment of utilities.

FIG. 19 illustrates the role of an Adaptive Learning Manager in the system, specifically using a text message for feedback and detecting that there is no beneficial impact, and in response, decreasing the utility of the Text Message class based on the lack of favorable improvement.

Generally, the Adaptive Learning Manager 68 correlates the messages that the IDA Dialog Manager sends with whether subsequent data measurements are within their pre-specified limits. Utility is decreased for message classes that have a negative correlation or no correlation to improvements; utility is increased for message classes that have a positive correlation to improvements.

Figure 20:
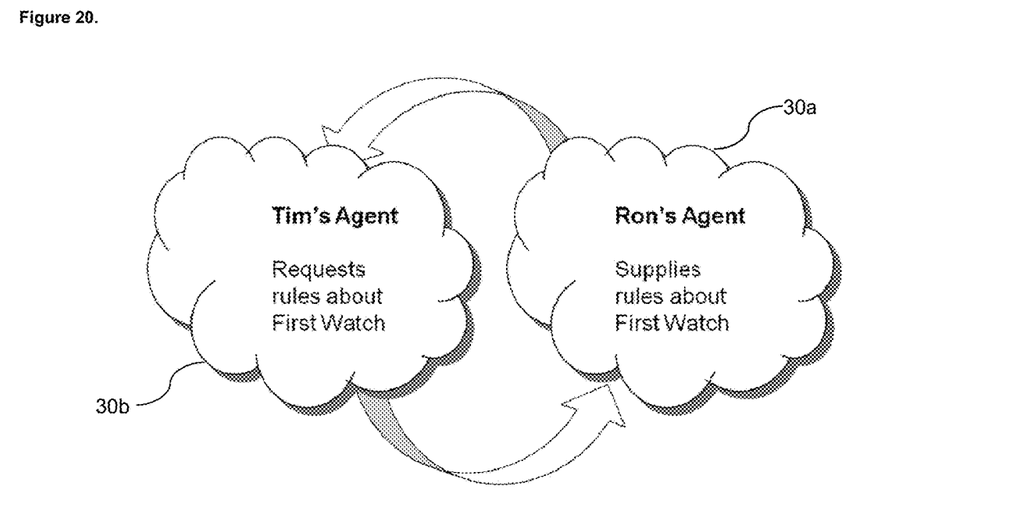
FIG. 20 illustrates a method of learning by the importation of rule systems from other users.

FIG. 20 illustrates another aspect of IDA's adaptive learning; the system can also learn from other systems by requesting rules on various topics. For example, if meals from a particular restaurant appear in the input from user Tim, relevant rules about that restaurant can be obtained from the rules 30a about that restaurant developed for Tim, to create rules 30b about that restaurant for user Ron.

CONCLUSION

This document describes a communications system that informs a user about the relationship between measurements and goals. For example, it informs a diabetic user whether his blood glucose is within or outside preset limits. The system is innovative in that it employs a wide range of communication strategies in a non-deterministic fashion so as to keep the user interested in the communications and be effective in offering advice. It also varies emphasis and the time of transmission again to avoid a monotonous sequence of communication. Finally, the system is adaptive and adjusts its decision making based on the success or failure of different modalities in affecting the user's behavior.

The present invention has been described in connection with several embodiments and some of those embodiments have been elaborated in substantial detail. However, the scope of the invention is not to be limited by these embodiments which are presented as exemplary and not exclusive. The scope of the invention being claimed is set forth by the following claims.

What is claimed is:

1. A computer implemented method for generating communications directed to a human user in response to data relevant to the human user,
   a. receiving data on measured quantities of interest to the user and storing said data in electronic memory,
   b. evaluating the data in a processor and creating notifications to be delivered to the human user regarding the measured quantities and the relationship of those quantities to goals and limits,
   c. the processor performing programmed steps selecting a message technique for communication to the human user in a non-deterministic fashion, based upon probabilistic selection criteria including a utility value associated with each of plural available message techniques, and
   d. using an electronic communication infrastructure, delivering a message to the human user regarding at least one of the measured quantities using the selected message technique.

2. The method of claim 1 further comprising performing an adaptive process to improve the effectiveness of the communications, the adaptive process altering the probabilistic selection criteria for message types in response to the response of the user to past uses of a message technique for communication to the user.

3. The method of claim 1 wherein an initial utility value for a user and a given message technique is generated based upon the average utility values of that technique for other users.

4. The method of claim 1 further comprising moderating potential overflow of messages to a user by the steps of placing messages in a queue, and applying rules to prune that queue by combining messages or cancelling messages.

5. The method of claim 1 further comprising adjusting a level of emphasis of a message based on trends in the measured quantities.

6. The method of claim 1 further comprising storing contact information for friends or family, and addressing messages to friends or family as collateral recipients.

7. The method of claim 6 wherein the addressing of messages to friends or family is responsive to the effect of prior messages upon at least one measured quantity.

8. The method of claim 1 wherein the messaging techniques include two or more of: email communications; SMS messages; instant messages; social network messages and social network postings.

9. The method of claim 8 wherein the selection of a message technique is responsive to the effect of prior messages using that technique upon at least one measured quantity.

10. The method of claim 1 further comprising receiving geolocation of a user, and selecting a message technique in response to geolocation data for the user.

11. The method of claim 10 wherein geolocation is used to determine whether the user is in a hands-busy environment, and in response employing audible message techniques.

12. The method of claim 1 further comprising receiving schedule information for a user and selecting a message technique in response to schedule information for the user.

13. The method of claim 12 wherein a quiet messaging technique is selected in response to determination that the user is in a quiet location.

14. The method of claim 1, wherein the measured quantities comprise two or more of blood glucose, food intake, exercise activity, body weight, and medication intake in order to manage blood glucose.

* * * * *